(12) United States Patent
Ladizinsky

(10) Patent No.: US 9,572,757 B2
(45) Date of Patent: Feb. 21, 2017

(54) METHOD FOR OXYGEN TREATMENT OF INTACT SKIN

(71) Applicant: Avent, Inc., Alpharetta, GA (US)

(72) Inventor: Daniel A. Ladizinsky, Lake Oswego, OR (US)

(73) Assignee: Daniel A. Ladizinsky, Lake Oswego, OR (US)

( * ) Notice: Subject to any disclaimer, the term of this patent is extended or adjusted under 35 U.S.C. 154(b) by 0 days.

(21) Appl. No.: 14/702,843

(22) Filed: May 4, 2015

(65) Prior Publication Data

US 2015/0238396 A1  Aug. 27, 2015

Related U.S. Application Data

(63) Continuation of application No. 13/535,803, filed on Jun. 28, 2012, now Pat. No. 9,044,462, which is a continuation-in-part of application No. 12/273,698, filed on Nov. 19, 2008, now abandoned, which is a continuation of application No. 11/269,433, filed on Nov. 8, 2005, now abandoned.

(60) Provisional application No. 60/634,322, filed on Dec. 8, 2004.

(51) Int. Cl.
| | |
|---|---|
| *A61K 8/02* | (2006.01) |
| *A61K 8/22* | (2006.01) |
| *A61Q 19/00* | (2006.01) |
| *A61K 33/40* | (2006.01) |
| *A61K 45/06* | (2006.01) |
| *A61K 8/04* | (2006.01) |
| *A61K 8/19* | (2006.01) |
| *A61Q 19/08* | (2006.01) |

(52) U.S. Cl.
CPC .............. *A61K 8/22* (2013.01); *A61K 8/0208* (2013.01); *A61K 8/042* (2013.01); *A61K 8/19* (2013.01); *A61K 33/40* (2013.01); *A61K 45/06* (2013.01); *A61Q 19/00* (2013.01); *A61Q 19/08* (2013.01); *A61K 2800/28* (2013.01); *A61K 2800/882* (2013.01)

(58) Field of Classification Search
None
See application file for complete search history.

(56) References Cited

U.S. PATENT DOCUMENTS

| | | |
|---|---|---|
| 4,193,813 A | 3/1980 | Chvapil |
| 4,328,799 A | 5/1982 | LoPiano |
| 4,374,232 A | 2/1983 | Davis |
| 4,474,571 A | 10/1984 | Lasley |
| 4,608,041 A | 8/1986 | Nielsen |
| 4,624,656 A | 11/1986 | Clark et al. |
| 4,703,108 A | 10/1987 | Silver et al. |
| 4,801,291 A | 1/1989 | Loori |
| 4,969,881 A | 11/1990 | Viesturs |
| 5,021,160 A | 6/1991 | Wolpert |
| 5,032,400 A | 7/1991 | Wiersum et al. |
| 5,086,620 A | 2/1992 | Spears |
| 5,126,189 A | 6/1992 | Tanny et al. |
| 5,151,189 A | 9/1992 | Hue et al. |
| 5,269,931 A | 12/1993 | Hue et al. |
| 5,277,812 A | 1/1994 | Hue et al. |
| 5,407,685 A | 4/1995 | Malchesky et al. |
| 5,736,582 A | 4/1998 | Devillez |
| 5,792,090 A | 8/1998 | Ladin |
| 5,855,570 A | 1/1999 | Scherson et al. |
| 5,958,984 A | 9/1999 | Devillez |
| 6,000,403 A | 12/1999 | Cantwell |
| 6,183,732 B1 | 2/2001 | Salmon |
| 6,890,553 B1 | 5/2005 | Sun et al. |
| 6,900,198 B2 | 5/2005 | Malfroy-Camine et al. |
| 6,936,267 B2 | 8/2005 | King |
| 7,311,660 B2 | 12/2007 | Gomez |
| 7,854,349 B2 | 12/2010 | Manivannan et al. |
| 2003/0232114 A1 | 12/2003 | Dekleva |
| 2006/0121101 A1 | 6/2006 | Ladizinsky |
| 2010/0183538 A1 | 7/2010 | Legere |

FOREIGN PATENT DOCUMENTS

| | | | |
|---|---|---|---|
| WO | WO 01/49258 A2 | 7/2001 | |
| WO | WO 03082392 A2 * | 10/2003 | ............. A61K 9/127 |

* cited by examiner

*Primary Examiner* — Abigail Fisher
(74) *Attorney, Agent, or Firm* — Dority & Manning, P.A.

(57) ABSTRACT

Oxygen therapy for healthy or inflamed but intact skin involves placing an oxygen-generating dressing onto the skin to be treated, the oxygen-generating bandage being a one-time use dressing capable of generating oxygen for only a short period of time, not to exceed about 4 hours.

17 Claims, No Drawings

METHOD FOR OXYGEN TREATMENT OF INTACT SKIN

CROSS-REFERENCE TO RELATED APPLICATIONS

This application is a continuation of U.S. application Ser. No. 13/535,803, filed Jun. 28, 2012, which is a continuation-in-part of U.S. application Ser. No. 12/273,698, filed Nov. 19, 2008 (abandoned), which is a continuation application of U.S. application Ser. No. 11/269,433, filed Nov. 8, 2005 (abandoned), which claims the benefit of U.S. Provisional Application Ser. No. 60/634,322, filed Dec. 8, 2004 (abandoned), priority to all of which are hereby claimed.

BACKGROUND OF THE INVENTION

1. Field of the Invention

The present invention relates to the field of materials and technologies for the delivery of oxygen to the surface of the skin, i.e. topical oxygen therapy. The present invention achieves high levels of skin oxygen in healthy or inflamed, intact skin by topical application to intact skin. The oxygen is absorbed transcutaneously through the outer epithelium and into the deeper dermal and subcutaneous layers. One purpose of having the oxygen delivered to the deeper layers of the skin and soft tissue is to promote and improve the overall health and appearance of the skin. Another purpose of this topical oxygen therapy is to treat skin inflammations, both therapeutically and preventatively.

DETAILED DESCRIPTION OF THE PREFERRED EMBODIMENT(S)

Living skin cells depend on oxygen for metabolic function and survival. The primary route of oxygen delivery to the skin is by way of the circulatory system. The circulatory system carries oxygenated blood to the sub dermal vascular plexus and then further superficially into the dermis via a capillary network. The oxygen then travels by diffusion outward to the waiting skin cells. Oxygen may also enter the skin via the transcutaneous route. Atmospheric oxygen almost exclusively supplies the outer 0.25-0.40 mm of the superficial skin. Oxygen levels are well maintained in the superficial dermis and epithelium during occlusion by an arterial blood pressure cuff, indicating the importance of the external supply of oxygen to the superficial skin layers.

There are many instances where skin oxygenation becomes inadequate either by reduced supply or increased demand. In aging, smoking, and scarring, there is an impediment in oxygen supplied by the circulation. In conditions of inflammation, there may be an increased demand for oxygen to aid the immune system in destroying skin pathogens.

Cigarette smoking creates, a chronic hypoxia in the skin. Carbon monoxide chronically present in the smoker's bloodstream avidly (100 fold greater) out-competes oxygen for hemoglobin binding sites, decreasing blood $O_2$ content, and therefore delivery of oxygen to the skin. Furthermore, nicotine causes peripheral vasoconstriction which mechanically impedes the flow of blood to the skin. The chronic effects of cigarette smoking are manifest early in the skin, where loss of dermal thickness leads to increased fine wrinkling as well as deep creases in the skin. The impaired oxygen delivery to the skin also reduces the function of the structures such as sebaceous glands, reducing the skin moisture level and leading to cracking and peeling. Often a smoker will appear much older than stated age in years.

The same process occurs with natural aging in nonsmokers, only more gradually. Aging effects are seen earlier in life in people with certain genetic skin types with a thinner dermis. It is known that African Americans possess a thicker dermis which takes much longer to show signs of skin aging and atrophy. Fair skinned Caucasians may show these changes decades earlier, Aged skin is functionally comprised with reduced circulatory capacity for reactive hyperemia (Xakellis). Aged skin is known to have reduced circulatory oxygen consumption (Dobeln) and experiences slower diffusion of oxygen through the plasma, further impeding oxygen delivery to the skin cells (Chisholm).

In conditions of inflammation, anaerobic skin bacteria can become pathogenic and lead to inflammatory lesions or pustules such as acne eruptions. In that setting, additional oxygen is needed by white blood cells for the production of oxygen radicals necessary for killing the causative anaerobic bacteria. Supplying the skin surface with high levels of oxygen can help this condition.

The need for oxygen to improve skin health has been the basis for the development of many predicate devices and treatments such as topical hydrogen peroxide, tetradecaoxygen (oxyferin) or fluorocarbon based topical therapies. The transcutaneous delivery of oxygen is impaired by the stratum corneum, the relatively impervious lipid rich outer layer of the epithelium. Certain agents, such as salicylic acid, that allow exfoliation and reduction of the thickness of the stratum corneum can be used to increase the amount of oxygen deliverable by the transcutaneous route. In addition, there are many other classes of material and treatments for skin health that can slow or reduce the aging process and these can be combined with a topical oxygen therapy for optimal skin health. These may include retinoids, humectants, surfactants, pigment regulators, sebum reducers, growth factors, or others.

Hyperbaric oxygen has long been used as treatment for gangrene and large area skin ulcers. Hyperbaric chambers have been used for such purposes, but are large and cumbersome, In addition, large body surface areas are exposed, where exposure may not be medically indicated or desirable. Localized hyperbaric chambers have also been proposed, for example in U.S. Pat. Nos. 4,328,799; 4,474,571; 4,624,656, and 4,801,291. These chambers are still unwieldy, however, and self-use by the patient is generally not possible. In addition, these chambers require a supply of pressured oxygen.

U.S. Pat. Nos. 4,608,041 and 4,969,881 disclose dressing-type constructions where oxygen gas is directed through holes or through an oxygen-permeable film for treatment of wounds or sores. Once again, a source of oxygen gas is necessary. A modification is disclosed in U.S. Pat. No. 6,000,403, where the dressing also includes a storage medium to enable hyperbaric oxygen concentrations over an extended period for treating skin lesions. Hydrogen peroxide and an activating agent may be used to supply oxygen. The activating agent may be hemoglobin from the open wound.

U.S. Pat. No. 5,736,582 discloses application of a dressing containing hydrogen peroxide together with other constituents which retard decomposition of the hydrogen peroxide, so that nascent oxygen may be delivered to the skin over long periods of time. However, continued exposure to hydrogen peroxide is deleterious to the skin.

U.S. Pat. No. 5,792,090, to the present inventor, describes dressings which intermittently provide oxygen to burns and ulcers through decomposition of hydrogen peroxide with a catalytic decomposing agent.

Treatment of burns, ulcers, and open wounds with oxygen, whether supplied as a gas or as a decomposition product, is thus well documented. However, the art has not recognized that treatment of what is normally regarded as healthy skin, of acne, or other skin conditions where the epithelium is intact, for example psoriasis, dermatitis, rashes, infection by fungi and dermatophytes, may be facilitated by supplying concentrations of oxygen for short periods.

Thus, for example, acne is generally caused by anaerobic bacteria in blocked pores of individuals. If allowed to rupture, scarring and disfigurement is possible, especially in individuals with chronic infections. It would be desirable to treat such anaerobic infections while the surrounding and overlying skin is still intact.

Moreover, in individuals with thin skin, poor circulation, or who smoke tobacco products, their "healthy" skin may age prematurely, developing wrinkles, "crows-feet" and similar signs of aging. It would be desirable to provide healthy skin with treatment to eliminate or mitigate such effects.

U.S. Pat. No. 6,936,267 discloses acne treating compositions which employ chlorine dioxide or a chlorine dioxide precursor. However, the effects of chlorine dioxide, a powerful oxidant and cytogen, are in general undesirable.

In U.S. Pat. No. 6,900,198 teaches that compounds containing peroxides and superoxides should be scrupulously avoided, and discloses compositions for topical and other means of administration which contain inhibitors of oxy-radical formation, in particular, so-called salen-metal complexes.

It would be desirable to provide a treatment regimen which is effective against intact skin inflammation, including acne. It would be further desirable to provide a treatment regiment which helps prevent the aging of "healthy" skin, and of other dermatologic inflammations and infections where the epithelium is substantially intact. These treatment regimens should avoid exposure of the dermis to high concentrations of peroxidic species for lengthy periods of time.

SUMMARY OF THE INVENTION

The present invention is directed to the delivery of transcutaneous oxygen to intact skin for the purpose of penetrating the deeper layers to improve skin health and appearance to the treat anaerobic skin infections such as acne, and other inflammations as well. The oxygen is produced catalytically at the skin surface at high levels in conditions of semi-occlusion to enhance penetration. The production of oxygen is limited in time, such that after a high level of oxygen is produced over no more than two hours, the reaction ceases and the skin oxygen level is allowed to return to basal physiological pretreatment levels.

DETAILED DESCRIPTION OF THE PREFERRED EMBODIMENT(S)

The invention thus pertains to the use of a dressing or "bandage" which may be applied to the dermis, and which generates oxygen over a limited time, without employing a supply of compressed oxygen gas, or generation of oxygen gas by electrolysis or electrochemical decomposition, but which rather contains a peroxide compound, preferably hydrogen peroxide, and a catalyst contained in the dressing which facilitates decomposition of the peroxide over a limited period of time. It is most preferable that at least 80% of the total decomposition of peroxide, as expressed relative to total oxygen production, take place in less than two hours.

The dressing of the present invention is applied to skin where wrinkles or other aging defects are to be mitigated or prevented, or to areas over and preferably surrounding inflamed intact skin including subdermal infections by anaerobic bacteria, such as acne, which includes, as defined herein, pimples and boils, or to inflamed or infected areas where the epithelium is substantially intact, i.e. "intact skin", either as a preventative or as a treatment to an existing condition.

The dressing is preferably supplied as a self-adhesive patch. The self-adhesive portion may be a pressure sensitive adhesive layer surrounding the active area of the dressing, or the active area itself, i.e. the area which contacts or abuts the area to be treated, may be self adhesive. Of course, non-adhesive dressings may be used in conjunction with conventional adhesive tape, "ACE bandages" or other securing means as well.

By the term "intact skin" is meant skin wherein the epithelium is substantially intact. Such skin may appear wrinkled or dried out, but is free of open sores or lesions of any appreciable extent. Greatest concern is with skin in the facial region, particularly the forehead, on the sides of the face adjacent to the eyes ("crows feet"), below the eyes ("circles"), and adjacent the mouth area. However, other areas are also indicated, for example the back of the hands, etc., wherever rejuvenation of the skin or minimization of wrinkles is desired.

For treatment or prevention of acne, it is desirable that the inflamed area be totally intact, the point of infection not having been ruptured, for example. However, in many cases, ruptured acne pimples, boils, etc., will "skin over" rapidly following an initial rupture. While the dressings of the invention are designed to mitigate scarring, etc., caused by ruptured acne, boils, etc., by decreasing or eliminating infection without rupture, they may be applied to those which have ruptured and are bleeding, oozing, etc., or as a preventative measure to individuals who are prone to acne. The treatment, for example, can be used on acne-prone areas to change the biology of *propionbacterium* acne, which will reduce the number of colonizing bacteria in the pores and therefore minimize pathogenic acne. Similar treatment and prevention is useful in other skin disorders as well.

A preferred embodiment of the present technology involves a topically applied gel that contains a bound catalyst. The gel could also contain other salutary agents for skin health, and desirably is not a gel which will absorb water from the skin, contributing to dehydration. The substrate is delivered to the gel on application and it reacts with the catalyst to generate high levels of oxygen. A semi-permeable film may be applied over the gel to create an occlusive environment, facilitating movement of the oxygen to the skin and not to the atmosphere. The high level of oxygen at the skin surface creates a gradient that allows for successful diffusion through the outer layers into the deeper tissues. This treatment may be used to reduce fine lines and wrinkles in aging skin and to improve the overall appearance of skin. This treatment may also be used for acne conditions.

The gel may be any gel or hydrocolloid which is capable of transporting oxygen, preferably one while is also capable of absorbing aqueous hydrogen peroxide. Such gels may be hydrophilic or hydrophobic, and numerous types are known by those skilled in the art, including, without limitation, gels produced from alginates, natural gums, polysaccharides, and proteins, for example careengan gum, gum tragacanth, gum acacia, starch, gelatin, and the like, as well as synthetic gels based on high molecular weight hydrophilic linear polymers such as polyacrylic acid homo and copolymers, polyvinylpyrrolidone, polyvinyl alcohol, polyoxyethylene polymers, and the like, and lightly crosslinked polymers such as polyacrylamides, crosslinked polyacrylic acid, polyvinyl alcohols, and polyacrylate polymers, etc. Hydrophobic gels include those of crosslinked (meth)acrylates, organopolysiloxanes, etc. These gels may have water or other humectants, emollients, etc., dispersed, absorbed, or dissolved within the gel to facilitate hydration.

The occlusive covering, i.e. that which is closest to the skin, in one embodiment of the subject invention, may be manufactured as an integral component of the dressing, optionally with a surrounding medical adhesive periphery to secure the dressing to the skin surface surrounding the area to be treated. Examples are, in particular, hydrogels formed using the following water soluble or water insoluble gums or resins, with or without known crosslinking agents: agarose, alkyl and hydroxyalkylcellulose, amylopectin, arabinoglactin, carboxymethylcellulose, carrageenan, eucheuma, fucoidan, furcellaran, gelatin, guar gum, gum agar, gum arabic, gum ghatti, gum karaya, gum tragacanth, hydroxethylcellulose, hydroxypropylcellulose, hypnea, keratin, laminaran, locust bean gum, pectin, polyacrylamide, poly (acrylic) acid and homologs, polyethylene glycol, poly(hydroxyalkyl methacrylate), polyvinyl alcohol, polyvinylpyrrolidone, propylene glycol alginate, starch and modified analogs, tamarind gum, N-vinyl lactam polysaccharides, and xantham gum. In addition, such hydrogels can also be formed by the copolymerization and crosslinking of both hydrophilic and hydrophobic monomers, such as hydroxyalkyl esters of acrylic and methacrylic acids, derivatives of acrylamide and methacrylamide, and N-vinyl-2-pyrrolidone, alkyl acrylates and methacrylates, vinyl acetate, acrylonitrile and styrene. A preferred hydrogel is INTRA SITE.® gel, available from Smith and Nephew, Inc.

The dressing of the subject invention preferably contains an oxygen permeable membrane between the epidermis and the source of chemically-derived oxygen. The oxygen permeable membrane may be a durable, particularly more highly cross-linked hydrogel, or may be manufactured of the same material as the oxygen source reservoir, for example an alginate or other hydrogel, thus performing the duties of both reservoir and oxygen permeable membrane concurrently. However, the oxygen permeable membrane is preferably a microporous membrane or polymer film capable of transmitting oxygen but preferably incapable or inefficient in transmitting ionic substances in solution such as peroxide ion, hydroxide ion, and heavy metal ions. The oxygen permeable membrane may also be abutted, preferably on the side located furthest from the skin, with a layer of ion exchange resin particles or powders, or other ion adsorbing media. Preferably used are hydrophobic microporous membranes such as microporous teflon membranes. Other suitable microporous hydrophobic membranes include the VERSAPOR.® hydrophobic membranes available from Gelman Sciences, Ann Arbor, Mich., and those disclosed in U.S. Pat. Nos. 4,374,232 and 5,126,189. Also suitable are microporous membranes which bear anionic or cationic charged sites, or both. Such microporous membranes are disclosed, for example, in U.S. Pat. No. 5,021,160 (acidic, for cation exchange), U.S. Pat. Nos. 5,151,189 and 5,269,931 (cationic, for anionic exchange), and U.S. Pat No. 5,277,812 (interpenetrating, suitable for ultrapure water).

When a gel is used, the gel preferably contains dispersed therein a peroxide decomposition catalyst, as disclosed for example by U.S. Pat. No. 5,792,090, incorporated herein by reference. A preferred decomposition catalyst is manganese dioxide. If the water absorbancy of the gel is high, hydrogen peroxide may be applied directly to the gel, or may be applied in the form of a reservoir, absorbant felt or gauze, etc. For example, the dressing may have a closeable opening or a septum for introduction of aqueous hydrogen peroxide, or the peroxide solution may be maintained in a breakable ("rupturable") but sealed pouch within the dressing. The peroxide may also be encapsulated within polymer beads which will rupture upon application of pressure.

The dressing preferably is a topically applied gel which is prepared by admixing a peroxide-containing gel as described herein and a peroxide decomposition catalyst-containing gel as described herein. Since these gels will generate oxygen upon contact or admixture, it is clear to one skilled in the art that the gels must be stored apart from each other and admixed prior to topical application. It is further clear that the gels cannot merely contact each other, as in such cases the slow diffusion of the peroxide and catalyst will not allow for 80% of oxygen to be generated within a four hour period, preferably a two hour period. "Topical gel" is used in its customary medical, pharmaceutical, and cosmetic usage as a cream or lotion which can be applied by the fingers, a brush, swab, cotton ball, spatula, etc. The first and second gels are advantageously contained in separate compartments of a single container, and are preferably mixed together upon exit from the container.

The amount of solid catalyst utilized may be easily selected by routine experimentation, taking into account first, the oxygen source charge (amount and concentration) and the desired time of oxygenation; and second, the activity of the catalyst, its state of subdivision, and the diffusion rates of the containing material used. Solid catalysts have activities proportional to their surface area, for example, and thus finely divided manganese dioxide powder will decompose a fixed amount of hydrogen peroxide at a much greater rate than coarse manganese dioxide granules. Moreover, if the manganese dioxide is encompassed within a gel, the decomposition rate will be lowered, as the rate will be dependent upon the rate of diffusion of hydrogen peroxide into the gel. The containing gel may also perform the function of absorbing the peroxide oxygen precursor. Amounts of manganese dioxide in powder form of about 20 μg/cm$^2$ of dressing area are suitable. Potassium permanganate applied in solution form to result in from 1-30 μm/cm$^2$ are also suitable. The amount of catalyst may be determined in any given case through routine experimentation.

The decomposition catalyst may be contained within a foam. For example, an open-celled polyurethane foam may be prepared by reacting an isocyanate component with a polyol component, one or both of the latter containing ground manganese dioxide. The oxygen source, i.e. hydrogen peroxide, may then be absorbed into the foam whereupon it will be decomposed to produce oxygen. Likewise, other foams, including those of biologically derived materials, such as collagen sponge prepared by the method of U.S. Pat. Nos. 4,193,813 or 4,703,108 may be used.

Another preferred embodiment of the present technology comprises a "patch" that may be fixed by adhesive edges to certain anatomic areas of the face, such as the lower eyelid or lateral orbital rim region (crow's feet area), and to cover acne problem areas. Fibers in the patch dressing may contain the bound catalyst that, when presented with substrate, would initiate a high level of oxygen production. The fibers may also contain other salutary agents for skin health. The patch could be discarded after 1-2 hours of usage or could be left on overnight if desired, as the beneficial agents within the dressing could have continued beneficial effects on the skin overnight.

For example, the fibers may be spun from spinnable polymer mixtures or dopes which contain finely dispersed manganese dioxide particles. The fibers are preferably water permeable or absorbable, for example of polyvinyl alcohol or polyacrylamide. Fibers coated or plated with decomposition catalysts may also be used.

The peroxide may be any peroxide which decomposes to produce oxygen, but should be a peroxide which either has no toxic decomposition products or whose decomposition products cannot reach the dermis because of the construction of the device. For example, the use of a very finely pored semipermeable membrane which allows oxygen and preferably water also to pass but which blocks larger molecules could be employed when the peroxide is one such as benzoyl peroxide. However, for cost reasons as well as avoidance of any chance of dermal contact with undesirable decomposition products, the preferred peroxide is hydrogen peroxide.

The hydrogen peroxide which is preferably used is generally supplied at a concentration of less than 10% by weight relative to the weight of the supply composition, preferably 0.5 to about 6 weight percent, and most preferably 2 to 6 weight percent. The hydrogen peroxide should be storage stable, whether supplied separately from the dressing in the form of an ampule or syringe, or incorporated in the dressing in a breakable pouch or other means. Standard methods of stabilizing the peroxide against its natural tendency to spontaneously decompose may be used. The peroxide may be supplied in a composition whose other ingredients are substantially water, or may be supplied in a composition containing gelling agents, solubilizers, humectants, etc. The amount supplied to the dressing or contained therein should be such that decomposition by the decomposition catalyst does not cause the dressing to rupture by building up excessive pressure. The amount should also be such that oxygen is not supplied in appreciable amounts for an extended period of time. From 80-90% of the hydrogen peroxide should decompose into oxygen, following activation, within no more than 4 hours, and preferably less than two hours. The remaining hydrogen peroxide, if any, should slowly decompose at a much reduced oxygen generating rate. The benefits of the invention are most notable when the majority of oxygen delivery takes place within a period of about two hours or less.

The oxygen source may be absorbed by the containing material, as described previously may be absorbed by a separate absorbing layer, or may be introduced into a chamber whose depth in a direction orthogonal to the wound surface dictates the volume of oxygen supplying solution to be administered.

For example, a separate hydrogel or open-celled foam layer may be used to absorb the oxygen supply solution. The thickness of this layer may be varied depending upon the time of treatment desired for a given catalyst amount and configuration. Alternatively, an initially empty space may be provided, with an opening closeable by adhesive tape or other closure device.

Because the peroxide concentration in preferred embodiments is low, and because toxic substances such as benzoyl peroxide will not contact the dermis or exude from the dressing, the dressing may be used in sensitive areas such as the vicinity of the eyes, for example to eliminate "crows feet" wrinkles. Bandages for this application are preferably somewhat triangular in shape, one vertex pointed in the direction of the eye. For wrinkles under the eye, for example the circular wrinkles or depressions often observed, the dressing may be in the form of a crescent, the concave side of which is closest to the eye.

After activation, the bandage may be removed after the period of maximum oxygen generation is over, but may also be left attached for extended periods, for example overnight. In such cases, it is desirable that the dressing be in the form of a gel containing water, humectants, softening agents, etc., as are customary in cosmetic applications. Examples of such substances include polypropylene glycol, dipropylene glycol, glyercine, glycerine esters, sorbitan esters, lanolin, etc. Other ingredients such as exfoliating agents, e.g. salicylic acid, surfactants, pigment regulators, sebum reducers, growth factors, vitamins, antibiotics, etc., may also be included.

The dressing also preferably includes a cover which is of relatively low permeability to oxygen, preferably a continuous polymer film. Since oxygen generation is only for a short time, complete impermeability is not required, and films which allow some escape of oxygen can be used. Preferred films are those of polyethylene, polypropylene, polyvinyl chloride polystyrene, polyester, polyamide, and the like. Such films are well known and are readily available from numerous sources.

Thus, the present invention pertains to dressings which are capable of delivering oxygen to the skin surface once, for a limited period of time, and to a method of treating oxygen-depleted skin and/or skin infections or lesions by applying such a dressing. The invention is particularly useful for treating skin which has been damaged by oxygen deprivation, including skin which has wrinkled, and common disorders resulting from infection by anaerobic or aerobic bacteria such as pimples, boils, and acne, as well as treatment for preventing inflamation, acne, and the like.

The devices may include a reservoir which may be an absorbent fibrous structure or a gel, the reservoir containing a peroxide such as hydrogen peroxide which is decomposable to release oxygen. The peroxide may be added to the dressing just prior to application to the dermis, or may be contained in the dressing in the form of a rupturable pouch, for example of thin-walled plastics material.

The dressing's reservoir substance may also be a solid or liquid which readily forms a gel upon being acted upon by water or by a hydrogen peroxide solution. The gel or other reservoir material may directly contact the skin and may be self adhesive, or may be isolated from the skin by an oxygen- and preferably also moisture-permeable membrane, such as a microporous polymer film. Such films are available commercially from companies such as a Millipore, etc.

The dressing preferably is surrounded along its periphery by an adhesive border which facilitates temporary adhesion to the skin when the membrane or reservoir is not self adhesive. When a rupturable pouch of oxygen-generating chemical is contained in the dressing, it is preferably located on the side of the reservoir remote from the side of the dressing to be applied to the skin, and is preferably surmounted by an impervious cover material capable of maintaining all components within the dressing per se.

When hydrogen peroxide or other peroxides are employed, the peroxide may also contain an inhibitor to minimize loss of hydrogen peroxide by decomposition during storage, and may further contain one or more antioxidants to prevent formation of superoxide ions. Such antioxidants are well known, and include, for example but not by limitation, hindered phenols such as those available from Ciba Geigy, and common antioxidants such as di(t-butyl) cresol and di(t-butyl)phenol.

While embodiments of the invention have been illustrated and described, it is not intended that these embodiments illustrate and describe all possible forms of the invention. Rather, the words used in the specification are words of description rather than limitation, and it is understood that various changes may be made without departing from the spirit and scope of the invention.

What is claimed is:

1. A method of treating intact skin, comprising:
applying to an area of skin to be treated, an oxygen generating, one time use dressing comprising a first gel containing a peroxide decomposition catalyst and a rupturable reservoir containing a peroxide, wherein said rupturable reservoir comprises a second gel, wherein the peroxide decomposition catalyst decomposes the peroxide to generate oxygen upon contact between the first gel and the peroxide after the reservoir is ruptured, said dressing having a layer which is impermeable to oxygen disposed on an outer surface remote from a skin contacting surface, wherein 80% or more of the peroxide is decomposed into oxygen, further wherein oxygen is delivered over a period of about 2 to 4 hours.

2. The method of claim 1, wherein said dressing further comprises a pressure sensitive adhesive which reversibly bonds to the skin.

3. The method of claim 1, wherein said peroxide decomposition catalyst comprises manganese dioxide.

4. The method of claim 1, wherein said first gel comprises alginate, carageenan gum, gum tragacanth, gum acacia, starch, gelatin, polyacrylic acid, polyvinylpyrollidone, polyvinyl alcohol, polyoxyethylene, polyacrylamide, crosslinked polyacrylic acid, polyvinyl alcohol, polyacrylate, crosslinked (meth)acrylate, or organopolysiloxane.

5. The method of claim 1, wherein said peroxide is hydrogen peroxide.

6. The method of claim 5, wherein the second gel contains said hydrogen peroxide in an amount of less than 6 weight percent.

7. The method of claim 5, wherein the second gel contains said hydrogen peroxide in an amount of from 0.5 weight percent to 6 weight percent.

8. The method of claim 1, wherein said intact skin is inflamed skin, dry skin, wrinkled skin, hypoxic skin, or a combination thereof.

9. The method of claim 1, wherein said intact skin is adjacent an ocular region.

10. The method of claims 9, wherein the skin is characterized by crows feet, wrinkles or circles under the eyes.

11. The method of claim 1, wherein said intact skin is characterized by the presence of acne or rosacea.

12. An oxygen generating, one time use dressing for treating intact skin, the dressing comprising a first gel containing a peroxide decomposition catalyst and a rupturable reservoir containing a peroxide, wherein the rupturable reservoir comprises a second gel, wherein the peroxide decomposition catalyst decomposes the peroxide to generate oxygen upon contact between the first gel and the peroxide after the reservoir is ruptured, said dressing having a layer which is impermeable to oxygen disposed on an outer surface remote from a skin contacting surface, wherein 80% or more of the peroxide is decomposed into oxygen, further wherein oxygen is delivered over a period of about 2 to 4 hours.

13. The dressing of claim 12, wherein said dressing further comprises a pressure sensitive adhesive which reversibly bonds to the skin.

14. The dressing of claim 12, wherein said peroxide decomposition catalyst comprises manganese dioxide.

15. The dressing of claim 12, wherein said first gel comprises alginate, carrageenan gum, gum tragacanth, gum acacia, starch, gelatin, polyacrylic acid, polyvinylpyrollidone, polyvinyl alcohol, polyoxyethylene, polyacrylamide, crosslinked polyacrylic acid, polyvinyl alcohol, polyacrylate, crosslinked (meth)acrylate, or organopolysiloxane.

16. The dressing of claim 12, wherein the second gel contains said peroxide in an amount of less than 6 weight percent, wherein said peroxide is hydrogen peroxide.

17. The dressing of claim 12, wherein the second gel contains said peroxide in an amount of from 0.5 weight percent to 6 weight percent, wherein said peroxide is hydrogen peroxide.

* * * * *